United States Patent
Wirkner

(10) Patent No.: US 9,902,338 B2
(45) Date of Patent: Feb. 27, 2018

(54) RETAINING APPARATUS FOR A MOBILE DEVICE

(71) Applicant: WIRKNER GMBH, Bietigheim-Bissingen (DE)

(72) Inventor: Marco Wirkner, Bietigheim-Bissingen (DE)

(73) Assignee: WIRKNER GMBH, Bietigheim-Bissingen (DE)

( * ) Notice: Subject to any disclaimer, the term of this patent is extended or adjusted under 35 U.S.C. 154(b) by 40 days.

(21) Appl. No.: 14/891,407

(22) PCT Filed: May 15, 2014

(86) PCT No.: PCT/EP2014/059974
§ 371 (c)(1),
(2) Date: Nov. 16, 2015

(87) PCT Pub. No.: WO2014/184301
PCT Pub. Date: Nov. 20, 2014

(65) Prior Publication Data
US 2016/0082895 A1  Mar. 24, 2016

(30) Foreign Application Priority Data
May 15, 2013 (DE) .................. 10 2013 008 303

(51) Int. Cl.
*B60R 11/02* (2006.01)
*B60R 7/04* (2006.01)
*B60R 11/00* (2006.01)

(52) U.S. Cl.
CPC ............ *B60R 11/0241* (2013.01); *B60R 7/04* (2013.01); *B60R 2011/0007* (2013.01); *B60R 2011/0075* (2013.01); *B60R 2011/0084* (2013.01)

(58) Field of Classification Search
CPC ......... B60R 11/0241; B60R 2011/0075; B60R 2011/0007; B60R 7/04
(Continued)

(56) References Cited

U.S. PATENT DOCUMENTS 5,556,017 A * 9/1996 Troy .................. B60R 11/0241
224/275
5,836,496 A * 11/1998 Levin ................. B60R 11/0241
224/275

(Continued)

FOREIGN PATENT DOCUMENTS

DE 102011055195 A1 * 5/2013 ............ B60R 11/02
DE 102013000138 A1 * 7/2014 ............ B60R 11/02
(Continued)

*Primary Examiner* — Justin Larson
(74) *Attorney, Agent, or Firm* — McGlew and Tuttle, P.C.

(57) ABSTRACT

A holding device (5) for a mobile device (6) in a motor vehicle, which holding device is arranged so as to be easily accessible by vehicle occupants in the region of an interior furnishing item such as a control panel, a center console or the like in the passenger compartment (1) of the motor vehicle and includes a visible receiving element (7) for the mobile device, wherein the receiving element, by means of an insertion opening (8), surrounds a relatively slim housing body of the mobile device. To optimize the holding device, the receiving element has an insertion plate (11) which contains an orifice (34) of the insertion opening and can be inserted into an opening of the interior furnishing item.

15 Claims, 5 Drawing Sheets

(58) Field of Classification Search
USPC ................................ 224/929, 483; 248/27.1
See application file for complete search history.

(56) References Cited

U.S. PATENT DOCUMENTS

| | | | | |
|---|---|---|---|---|
| 5,996,866 A * | 12/1999 | Susko | ................ | B60R 11/0241 224/281 |
| 6,049,288 A * | 4/2000 | Kawasaki | ............. | B60K 37/00 248/27.1 |
| 6,056,175 A * | 5/2000 | Mieglitz | ................ | B60K 37/04 224/282 |
| 6,354,649 B1 * | 3/2002 | Lee | ........................ | B60K 37/02 185/39 |
| 7,494,033 B2 * | 2/2009 | Kaiser | ..................... | B60R 7/046 224/542 |
| 7,510,241 B2 * | 3/2009 | Nathan | .................. | B60K 35/00 248/284.1 |
| 7,665,709 B2 * | 2/2010 | Cvek | .................... | A47B 21/007 108/25 |
| 7,900,988 B2 * | 3/2011 | Ryu | .................... | B60R 11/0235 224/483 |
| 8,233,269 B2 * | 7/2012 | Hotary | .................. | B60K 35/00 248/27.1 |
| 8,544,927 B2 * | 10/2013 | Clochard | ................ | B60R 11/02 224/483 |
| 8,550,529 B2 * | 10/2013 | Clochard | ................ | B60R 11/02 224/483 |
| 8,624,547 B2 * | 1/2014 | Thorsell | ................ | B60N 3/002 320/107 |
| 8,955,728 B2 * | 2/2015 | Schultze | ................ | B62J 9/008 224/413 |
| 9,162,627 B2 * | 10/2015 | Greiner | .................... | B60R 7/08 |
| 9,270,318 B2 * | 2/2016 | Rassent | ................ | H04B 1/3877 |
| 9,469,253 B2 * | 10/2016 | Brunard | .................. | B60R 11/02 |
| 9,537,990 B2 * | 1/2017 | Vourlat | ............... | B60R 11/0235 |
| 2009/0152418 A1 * | 6/2009 | Bury | .................... | B60R 11/0235 248/205.3 |
| 2011/0157801 A1 * | 6/2011 | Satterfield | ............. | G06F 1/1607 361/679.01 |
| 2014/0223065 A1 * | 8/2014 | Jolda | ....................... | G06F 13/36 710/303 |
| 2015/0222313 A1 * | 8/2015 | Rassent | ................ | H04B 1/3877 455/575.9 |
| 2016/0082895 A1 * | 3/2016 | Wirkner | ............. | B60R 11/0241 224/544 |
| 2016/0311378 A1 * | 10/2016 | LaFargue | ............. | H04B 1/3877 |
| 2017/0028934 A1 * | 2/2017 | Helot | ..................... | B60R 16/03 |
| 2017/0072873 A1 * | 3/2017 | Brunard | ............. | B60R 11/0241 |

FOREIGN PATENT DOCUMENTS

| | | |
|---|---|---|
| EP | 1 598 640 A1 | 11/2005 |
| EP | 2 249 347 A1 | 11/2010 |
| EP | 2 249 347 B1 | 3/2012 |
| JP | H11 91451 A | 4/1999 |

* cited by examiner

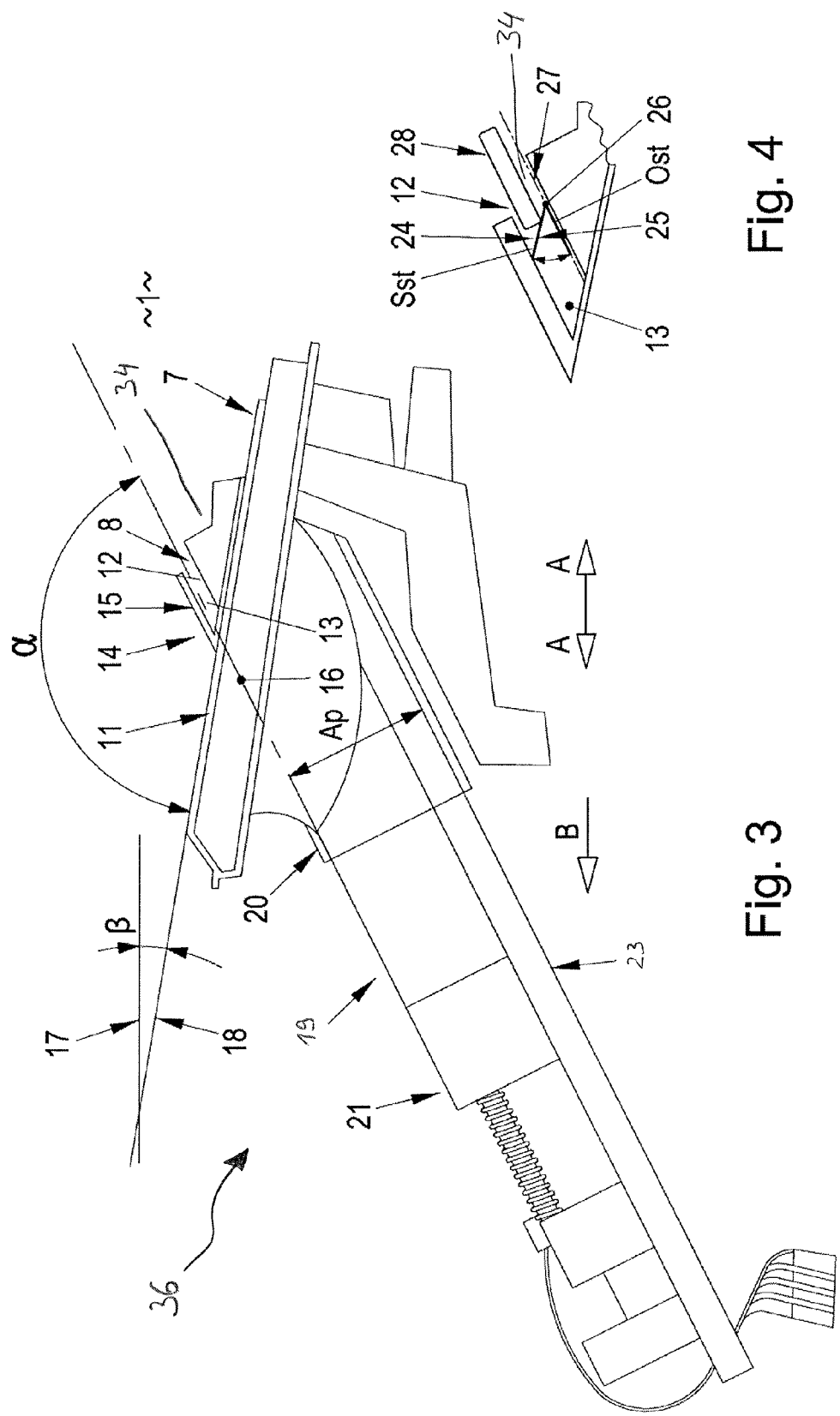

RETAINING APPARATUS FOR A MOBILE DEVICE

CROSS REFERENCE TO RELATED APPLICATIONS

This application is a United States National Phase Application of International Application PCT/EP2014/059974 filed May 15, 2014 and claims the benefit of priority under 35 U.S.C. § 119 of German Patent Application 10 2013 008 303.6 filed May 15, 2013 the entire contents of which are incorporated herein by reference.

FIELD OF THE INVENTION

The present invention relates a retaining apparatus for a transportable mobile device, including a smartphone, in a motor vehicle.

BACKGROUND OF THE INVENTION

The carrying and operation of sound carriers or smartphones, such as e.g. iPhones, mobile telephones or the like, in a motor vehicle is a demand of the market, which is accounted for in many forms by retrofit solutions of the accessories trade. Limits are therefore placed on these solutions with respect to design options, because they are exposed to protruding components on interior equipment in the passenger compartment of the motor vehicle.

A fastening device known from EP 1 598 640 A1 is constructed for a navigation computer and a navigation system, which can be fastened in a motor vehicle. Moreover, a holder with a connection cable is provided, which holder has a mounting plate. This mounting plate is for example attached using double-sided adhesive tape on a dashboard or a different suitable surface of the motor vehicle.

EP 2 249 347 B1 discloses a digital player or playback-device interface device with interchangeable adapter. The adapter is provided with a through hole for introducing and removing a digital player or playback device. A first and a second engaging part is provided at both ends of the adapter. An adapter fixing or fastening element comprises a guide rib and a concavity on the undersurface or surface thereof. Furthermore, a fixing or fastening spring is attached in the concavity. A housing, which carries the adapter fixing or fastening element, is connected to the adapter.

SUMMARY OF THE INVENTION

It is the object of the invention to create a retaining apparatus for a mobile device, including a transportable sound carrier, that is to say preferably for a smartphone, in a motor vehicle, which stands out in particular due to a high-quality haptic and/or optical integration and is preferably characterised by a simple structural design and good functionality. In this case, it should however also be ensured that the retaining apparatus on the one hand complies with ergonomic considerations and on the other hand has design advantages.

This object is achieved by means of a retaining device according to the present invention.

The advantages mainly achieved using the invention are to be seen in the fact that the retaining device for the sound carrier or the handheld device, particularly smartphone, e.g. in the form of an iPhone, mobile telephone or the like, can be integrated in an exemplary manner into the interior equipment of the passenger compartment, wherein the central console or the control panel or the dashboard are suitable in particular for accommodating the retaining apparatus. The accommodating element of the retaining apparatus is to be highlighted in this context, which can be accommodated with the exemplarily designed insertion plate in an opening of the interior equipment. In this case, the insertion plate is expediently adapted to the opening in such a manner that the opening of the interior equipment is completely closed by the inserted insertion plate. In this case, the insertion plate contains an orifice of the insertion opening, through which the respective sound carrier can be inserted into the insertion opening.

Optionally, in an embodiment, the insertion plate can additionally have an annular mouth, which, together with the insertion plate, offers targeted design options for an aesthetic design, which fulfils requirements. The annular mouth comprises the orifice of the insertion opening at least to some extent and gives the occupants of the motor vehicle clear information for inserting the sound carrier. Optionally, it can have a web protruding above the insertion plate, which can be produced in one piece with the insertion plate. Beneficial, principally structural conditions result if the annular mouth or the web runs at an obtuse angle to the insertion plate and the angle between insertion plate and annular mouth or web is defined as a function of the angle of the insertion plate to a horizontal line. To this end, it is possible that the insertion plate is orientated in the installed state, viewed counter to the direction of travel, in a plane extending obliquely from above downwards and the insertion plate and the annular mouth or the web enclose an obtuse angle.

A convenient solution is achieved if the accommodating element is connected to a carrying device, which comprises a retaining and ejection mechanism. In particular, the accommodating element and the carrying device can consist of one part. For manufacturing reasons, the carrying device in the region of the accommodating element and the accommodating element itself can consist of plastic.

Furthermore, according to an advantageous embodiment, standards for the retaining device are set in that the accommodating element with carrying device is connected to the interior equipment by means of one or a plurality of quick connections, wherein the accommodating element and the carrying device can be combined to form a module, which can be fastened in the interior equipment by means of simple mounting handles.

Finally, a locking element can be arranged in the insertion opening or in the accommodating cross section of the retaining apparatus, which locking element can be adjusted between an open position and a closed position. The locking element in this case contributes in a targeted manner to the counteraction of incorrect insertion of objects, e.g. coins into the insertion opening.

Particularly advantageous in this case is an embodiment in which the locking element is designed as a planar flap and is arranged in the region of the orifice in a pivotable manner about a pivot axis, such that the locking element closes in its final position flush with the likewise planarly designed insertion plate. At the same time, thanks to the flap-shaped locking element, an optically attractive closure is realized for the orifice, which closes the orifice flush to the insertion plate when the sound carrier is pulled out or removed.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a schematic side view of the retaining apparatus, approximately in the direction of the arrow X in FIG. 1;

FIG. 4 is a view of detail Y of FIG. 3 on a larger scale, with a locking element;

DESCRIPTION OF THE PREFERRED EMBODIMENTS

Figure 1:
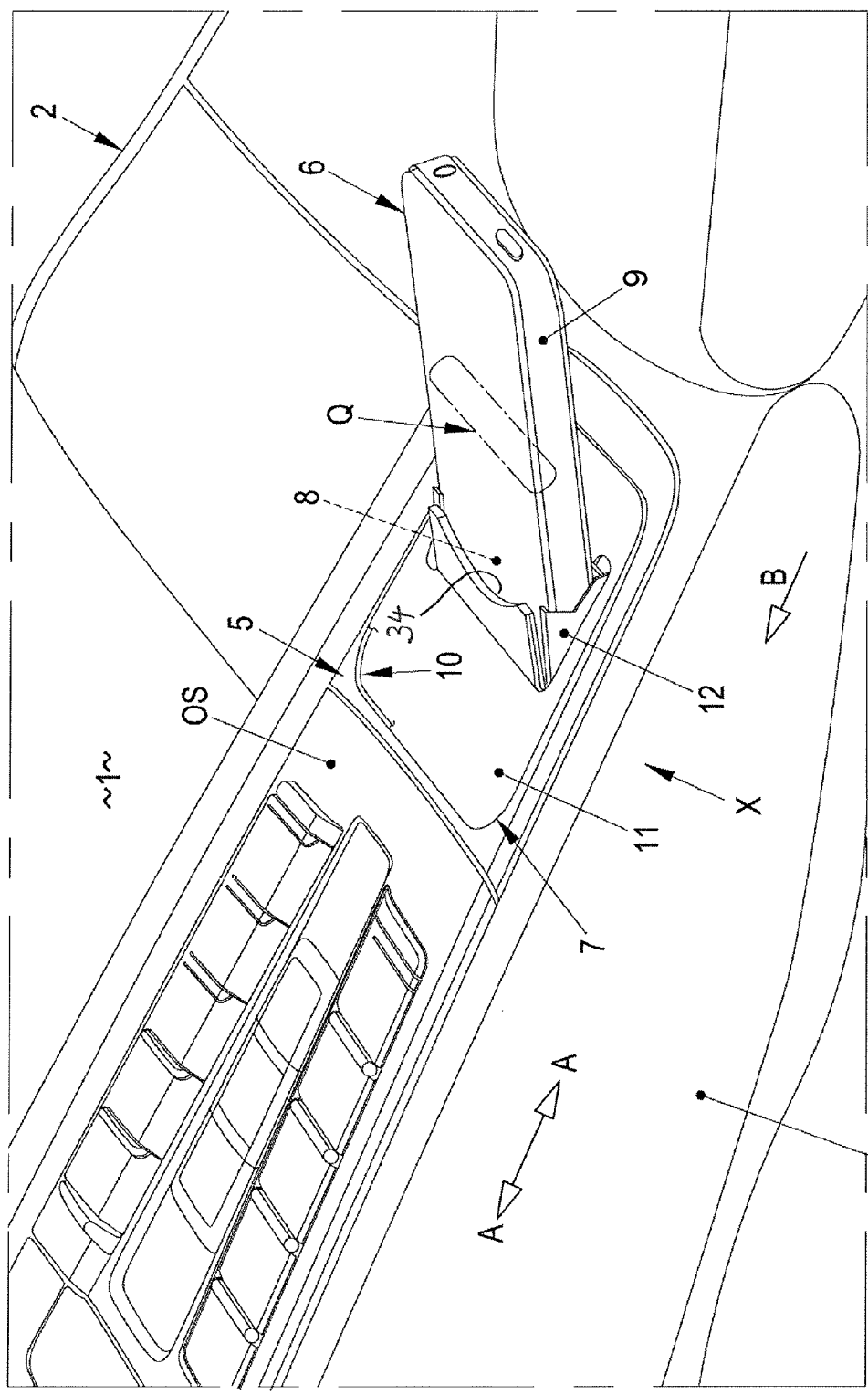
FIG. 1 is an oblique view of interior equipment in the form of a central console of a motor vehicle with a retaining device for a sound carrier, which assumes a pre-inserted position.

In a passenger compartment 1 of a motor vehicle, which is not illustrated in any more detail, a passenger seat 2 and a central console 3 are illustrated, which constitute components of interior equipment 4. This also includes a control panel, which is not depicted. In the exemplary embodiment, a retaining apparatus 5 for a transportable sound carrier (mobile device) 6, such as e.g. an iPhone, mobile telephone or the like is built into an upper side OS of the central console 3 of the interior equipment 4. The retaining apparatus 5 comprises an accommodating element 7 for the sound carrier 6, which can be seen well by occupants of the motor vehicle, wherein the accommodating element 7 encircles a relatively flat cross section Q of the housing body 9 of the sound carrier 6 with an insertion opening 8, when the sound carrier 6 is inserted into the insertion opening 8 at least to some extent.

Figure 2:
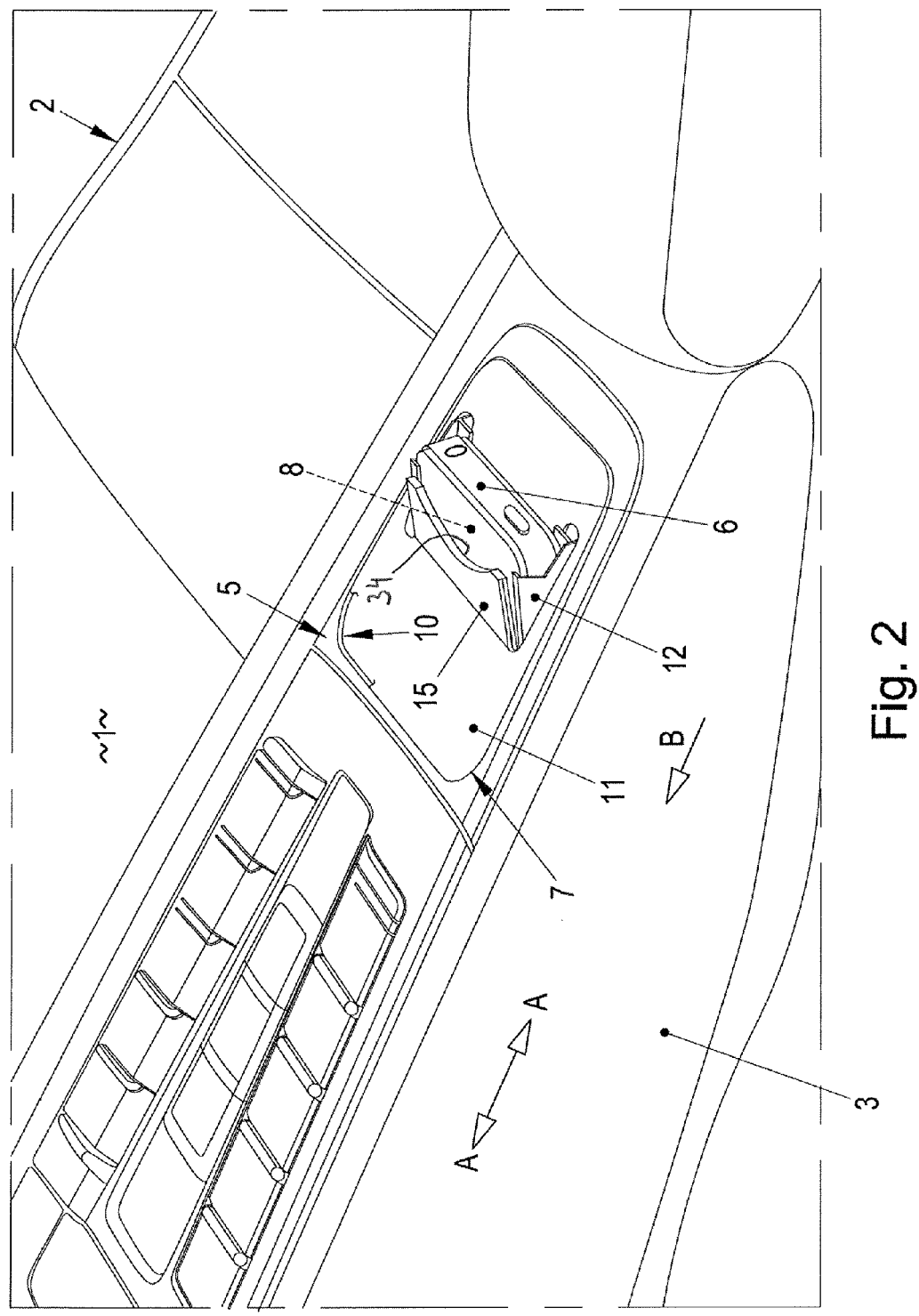
FIG. 2 is a view according to FIG. 2, but with the sound carrier in an inserted end position.

The accommodating element 7 has an insertion plate 11, which can be inserted into an opening 10 of the central console 3 of the interior equipment 4, which insertion plate is equipped, in the embodiments of FIGS. 1 and 2, with an annular mouth 12, which forms the insertion opening 8 at least in certain areas. The annular mouth 12 forms at least a part of an orifice 34 of the insertion opening 8. In the embodiment shown in FIG. 6, the orifice 34 is constructed directly at the insertion plate 11. In this embodiment, it is fundamentally possible to dispense with an annular mouth 12, which protrudes from a plane of the preferably planarly designed insertion plate 11.

The annular mouth 12 is formed by a U-shaped accommodating cross section 13 orientated transversely to the longitudinal direction of the vehicle A-A, which is integrated into the accommodating element 7 or the insertion plate 11. On a front side 14, in the direction of travel B, of the U-shaped accommodating cross section 13 of the annular mouth 12, the latter has a web 15, which is directed away from the insertion plate 11 in the direction of the passenger compartment 1.

According to FIG. 3, an angle α between the insertion plate 11 and a central longitudinal plane 16 of the U-shaped accommodating cross section 13 or the web 15 can be defined as a function of an angle β between the insertion plate 11 and a horizontal design plane 17 of the motor vehicle orientated in the longitudinal direction of the vehicle A-A. That is to say, a corresponding obtuse angle α (α>90°) results for a given acute angle β ((β<90°). If the acute angle β becomes larger, the obtuse angle α becomes smaller and vice versa. In the example, the two angles α and β are tuned to one another in such a manner that a sum of the two angles α and β is smaller than 180°. In particular, it is true that: α+β≤180°, where it is additionally true that: α>90° and β<90°. As viewed counter to the direction of travel B, the insertion plate 11 runs in a boundary plane 16 of the central console 3 extending obliquely from above downwards, specifically flush to the boundary plane 16.

The accommodating element 7 is connected to a carrying device 19, which has a retaining and an ejection mechanism 21 for the sound carrier 6. The constructive and functional design of the carrying device 19 is described thoroughly in EP 2 249 347 B1, which is cited at the beginning, the contents of which are incorporated herein by reference. According to FIG. 3, the accommodating element 7 is attached to the carrying device 19 by means of a connecting element 20. In this case, the central longitudinal plane 16 of the accommodating cross section 13 of the annular mouth 12 runs essentially with a parallel spacing Ap from a base plane 23 of the carrying device 19.

The accommodating element 7 and the carrying device 19 are held on the interior equipment 4 or the central console 3 by means of one or a plurality of quick connections. According to the example of FIG. 5, the quick connections have at least one clip apparatus 22, which is fastened e.g. on the accommodating element 7.

The accommodating element 7, the connecting element 20 and the carrying device 19 can be produced separately from one another and subsequently combined. It is also conceivable, however, to produce the aforementioned parts in one piece. It is furthermore possible to combine the accommodating element 7, the connecting element 18 and the carrying device 17 to form a module 23, which can be fastened in the interior equipment using simple mounting handles.

In FIG. 4, a locking element 24 is provided in the U-shaped accommodating cross section 13, which can be moved between a closed position Sst and an open position Ost. The sound carrier 6 inserted into the annular mouth 12 effects the open position Ost, specifically counter to the action of a leaf spring 25 of the locking element 24, which is connected via a film hinge 26 to a retaining part 27. In the closed position Sst of the locking element 24—the sound carrier 6 is not inserted—incorrect insertion of objects, e.g. coins 28 into the annular mouth 12 is counteracted.

Figure 6:
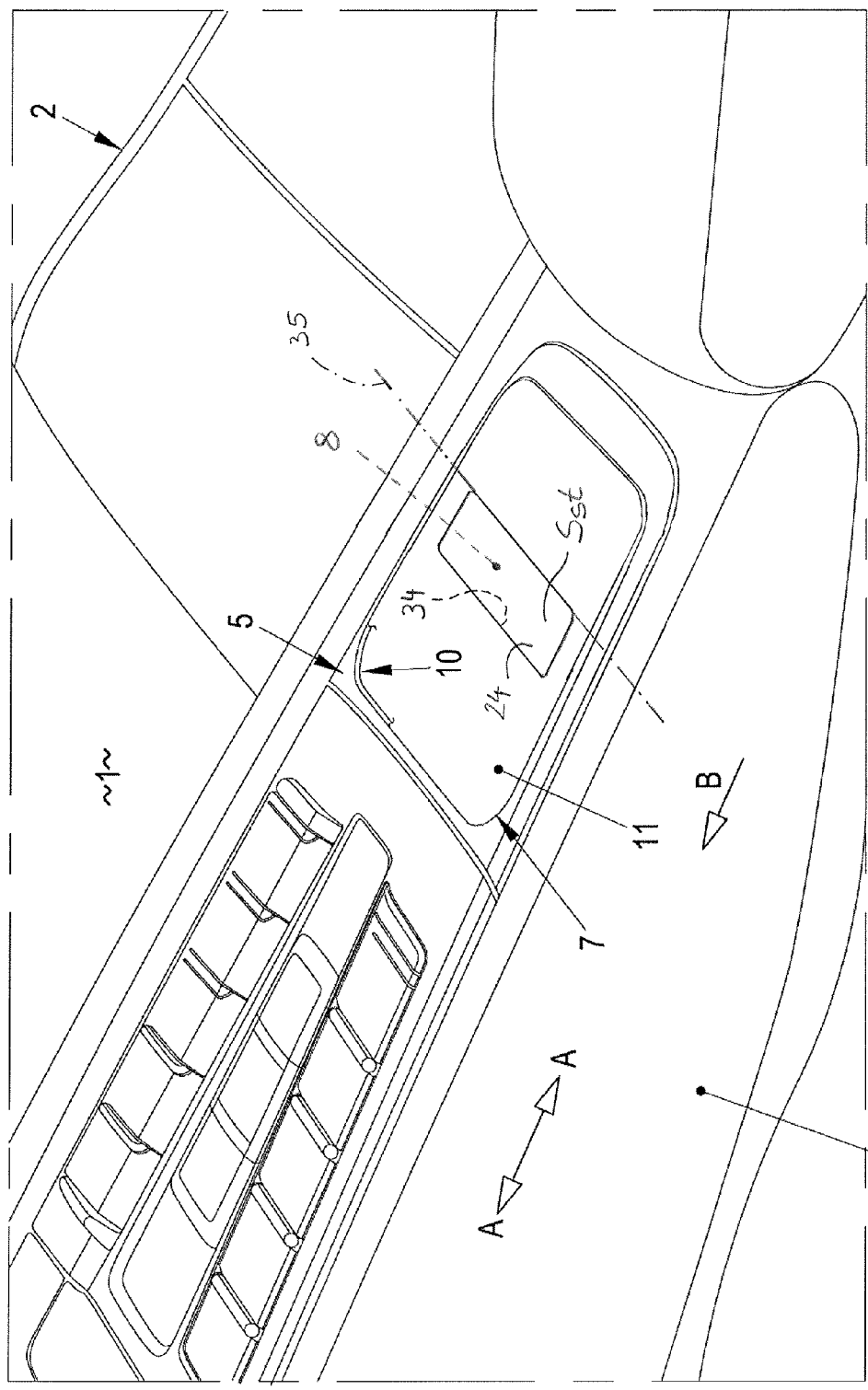
FIG. 6 is a view as in FIGS. 1 and 2, but with the sound carrier removed completely and also in a preferred embodiment.

Whilst in FIG. 4, the locking element 24 is arranged spaced from the orifice 34, virtually in the interior of the insertion opening 8, FIG. 6 shows a preferred embodiment, in which a pivot axis 35, about which the locking element 24 can be adjusted between the open position Ost and the closed position Sst, is arranged in the region of the orifice 34. This means that the locking element 24 closes the orifice 34 in its closed position Sst. In the example of FIG. 6, the locking element 24 is designed as a planar flap, which, in the closed position Sst, closes flush with the likewise planarly designed insertion plate 11. The closed position Sst is established automatically in a spring-loaded manner, when the sound carrier 6 or the smartphone is pulled out or removed.

Figure 5:
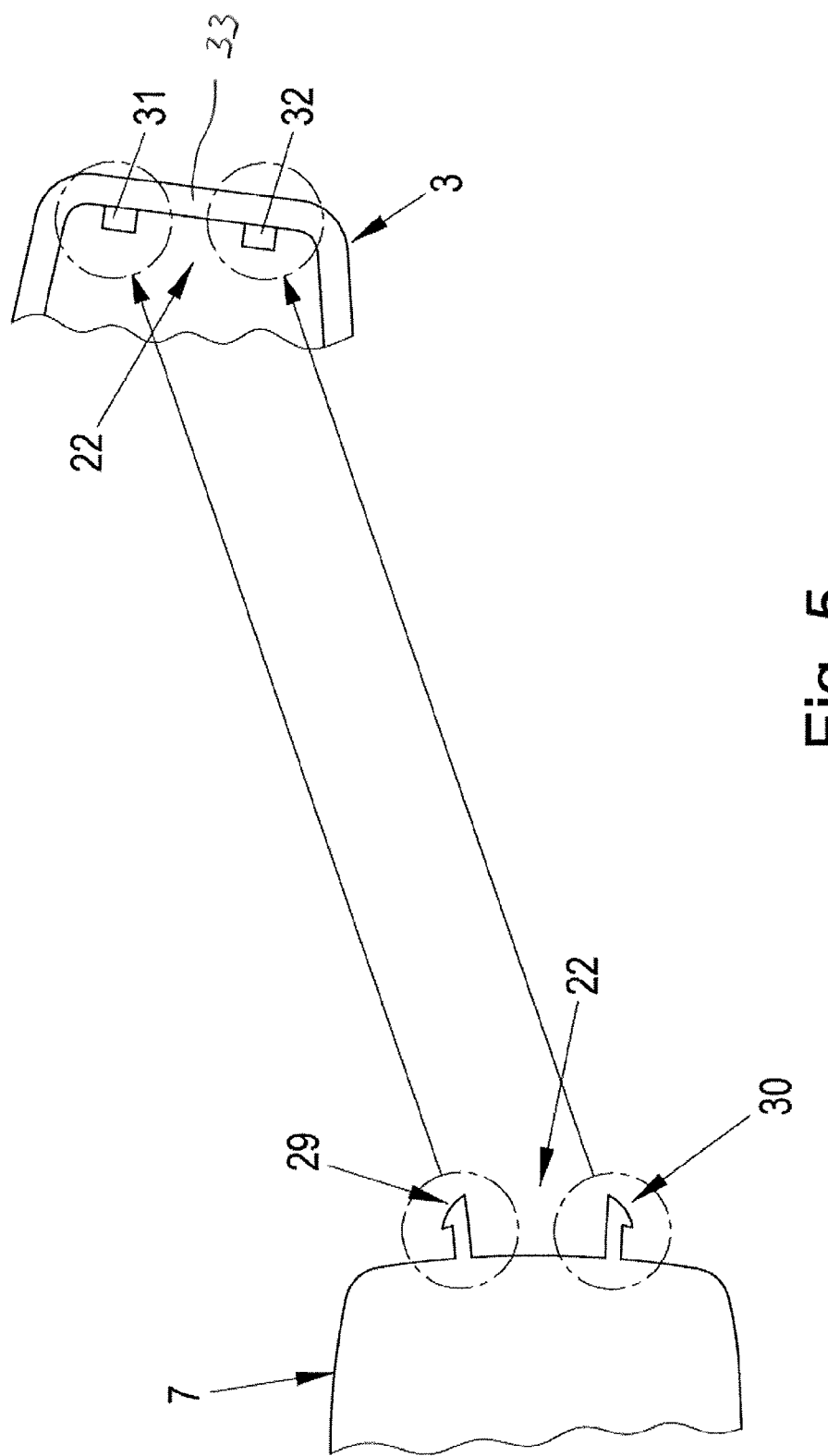
FIG. 5 is a view of a schematic illustration of a clip connection.

Finally, FIG. 5 reproduces the clip apparatus 22, which comprises clip hooks 29 and 30, which are spaced transversely to the longitudinal direction of the vehicle A-A, wherein the clip hooks 29 and 30 attached on the accommodating element 7 engage behind openings 31 and 32 in a fastening plate 33 of the central console 3.

While specific embodiments of the invention have been shown and described in detail to illustrate the application of the principles of the invention, it will be understood that the invention may be embodied otherwise without departing from such principles.

The invention claimed is:

1. A retaining apparatus for retaining a mobile device in a motor vehicle, wherein the retaining apparatus can be attached to be easily accessible for occupants of the motor vehicle in a region of interior equipment, such as a control panel, central console or the like, in a passenger compartment of the motor vehicle, the retaining apparatus comprising:
a visible accommodating element for the mobile device, wherein the accommodating element comprises an insertion opening, into which the mobile device can be inserted and which comprises a housing body of the mobile device, which is relatively flat in cross section, the accommodating element having an insertion plate, which contains the insertion opening and which can be inserted into an opening of the interior equipment, the accommodating element being connected to a carrying device, which has a retaining and ejection mechanism for the mobile device, wherein a connecting element is provided on a rear side of the insertion plate facing away from the passenger compartment in an installed state, said connecting element comprising the insertion opening.

2. The retaining apparatus according to claim 1, wherein a locking element, which can be moved between a closed position and an open position, is provided in the insertion opening, wherein the locking element, in the closed position, counteracts incorrect insertion of objects.

3. The retaining apparatus according to claim 2, wherein the locking element comprises a planar flap and the locking element is arranged in a region of the insertion opening in a pivotable manner about a pivot axis, such that the locking element closes in the closed position flush with the insertion plate, said insertion plate comprising a planar insertion plate.

4. The retaining apparatus according to claim 1, wherein the accommodating element is attached to the carrying device by means of a connecting element.

5. The retaining apparatus at least according to claim 4, wherein at least parts of the carrying device and the connecting element are produced one of separately from one another and in one piece.

6. The retaining apparatus at least according to claim 4, wherein the connecting element and the accommodating element are produced one of separately from one another and in one piece.

7. The retaining apparatus at least according to claim 4, wherein the accommodating element with the connecting element and the carrying device are combined to form a module, which can be connected to the interior equipment using simple mounting handles.

8. The retaining apparatus at least according to claim 4, wherein the accommodating element with the connecting element and the carrying device can be fixed on the interior equipment by means of one of a quick connection and a plurality of quick connections.

9. The retaining apparatus according to claim 8, wherein said one of said quick connection and the plurality of quick connections comprise at least one clip apparatus, which is held in position on the accommodating element.

10. The retaining apparatus according to claim 9, wherein the at least one clip apparatus comprises clip hooks, which are spaced transversely to a longitudinal direction of the vehicle, said clip hooks engaging behind openings in a fastening plate of the central console.

11. The retaining apparatus according to claim 1, wherein the insertion plate on a front side faces the passenger compartment in an installed state.

12. The retaining apparatus according to claim 11, wherein, as viewed counter to a direction of travel, the insertion plate in the installed state extends in a boundary plane of the central console extending obliquely from above downwards.

13. The retaining apparatus according to claim 11, wherein the insertion opening comprises a mobile device accommodating cross section orientated transversely to a longitudinal direction of the vehicle, which is integrated into the accommodating element.

14. The retaining apparatus according to claim 13, wherein the central longitudinal plane of the mobile device accommodating cross section of the insertion opening is orientated essentially with a parallel spacing from a base plane of a carrying device.

15. The retaining apparatus according to claim 13, wherein an angle between the insertion plate and a central longitudinal plane of the mobile device accommodating cross section is defined as a function of another angle between the insertion plate and a horizontal design plane in the motor vehicle, such that a sum of the angle and the another angle is less than or equal to 180°.

* * * * *